US00PP37451P2

(12) United States Plant Patent
Janes

(10) Patent No.: US PP37,451 P2
(45) Date of Patent: Jun. 2, 2026

(54) ***VERONICA* PLANT NAMED 'Balskywlipi'**

(50) Latin Name: ***Veronica* hybrid**
Varietal Denomination: Balskywlipi

(71) Applicant: Ball Horticultural Company, West Chicago, IL (US)

(72) Inventor: Jessica Diane Janes, Elkton, MD (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/349,733

(22) Filed: Oct. 3, 2025

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251
See application file for complete search history.

(56) References Cited

U.S. PATENT DOCUMENTS

PP25,748 P3 * 7/2015 Dobres ..... A01H 6/68
Plt./251

* cited by examiner

*Primary Examiner* — Susan Mccormick Ewoldt
(74) *Attorney, Agent, or Firm* — Megan Bowman

(57) ABSTRACT

A new and distinct cultivar of *Veronica* plant named 'Balskywlipi', characterized by its light, purplish-pink flowers, medium, green-colored foliage, and moderately vigorous, compact, upright-compact growth habit, is disclosed.

1 Drawing Sheet

Latin name of genus and species of plant claimed: *Veronica* hybrid.

Variety denomination: 'Balskywlipi'.

BACKGROUND OF THE INVENTION

The present invention relates to a new and distinct cultivar of *Veronica* plant botanically known as *Veronica* hybrid and hereinafter referred to by the cultivar name 'Balskywlipi'.

The new cultivar originated in a controlled breeding program in Cochranville, Pennsylvania, during November 2016. The objective of the breeding program was the development of *Veronica* cultivars with increased flower spikes, powdery mildew resistance and a compact, upright-mounded growth habit.

The new *Veronica* cultivar was the result of cross-pollination. The female parent of the new cultivar is a proprietary *Veronica spicata* breeding selection, coded X14-6480-004, unpatented, characterized by its medium, pink-colored flowers, medium, green-colored foliage, and moderately vigorous, compact growth habit. The male parent of the new cultivar is *Veronica spicata* 'Alllove', U.S. Plant Pat. No. 21,478, characterized by its pink-colored flowers, medium, green-colored foliage, and moderately vigorous, spreading growth habit. The new cultivar was discovered and selected as a single flowering plant within the progeny of the above stated cross-pollination during June 2019 in a controlled environment in Cochranville, Pennsylvania.

Asexual reproduction of the new cultivar by terminal stem cuttings since June 2019 in Cochranville, Pennsylvania and Elburn, Illinois has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balskywlipi' as a new and distinct cultivar of *Veronica* plant:

1. Light, purplish-pink colored flowers.
2. Medium, green-colored foliage; and
3. Moderately vigorous, upright-compact growth habit.

Plants of the new cultivar differ from plants of the female parent primarily in having light pink flowers and an upright habit. Plants of the new cultivar differ from plants of the male parent primarily in having light pink flowers and a dense, upright, and well-branched habit. Of the many commercially available *Veronica* cultivars, the most similar in comparison to the new cultivar is Moody Blues Pink 'Novaverpin', U.S. Plant Pat. No. 25,748. However, in side-by-side comparisons, plants of the new cultivar differ from plants of 'Novaverpin' in at least the following characteristics:

1. Plants of the new cultivar have a lighter flower color than plants of 'Novaverpin'.
2. Plants of the new cultivar have more branches per plant than plants of 'Novaverpin'; and
3. Plants of the new cultivar have longer leaves than plants of 'Novaverpin'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balskywlipi'. The plants were approximately six months old. The plants were grown as three plants per pot in one-gallon containers for approximately 10 weeks in a greenhouse in West Chicago, Illinois followed by 3.5 months in an outdoor nursery in West Chicago, Illinois. Plants were given one pinch three weeks before transplant and one pinch three weeks after transplant.

DETAILED BOTANICAL DESCRIPTION

Figure 1:
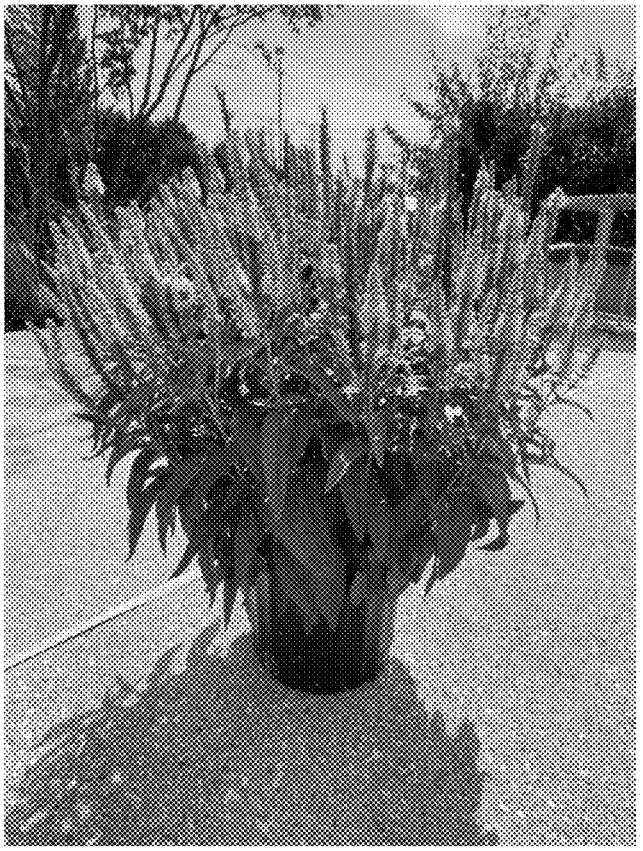
FIG. 1 illustrates a side view of the overall growth and flowering habit of 'Balskywlipi'.
Figure 2:
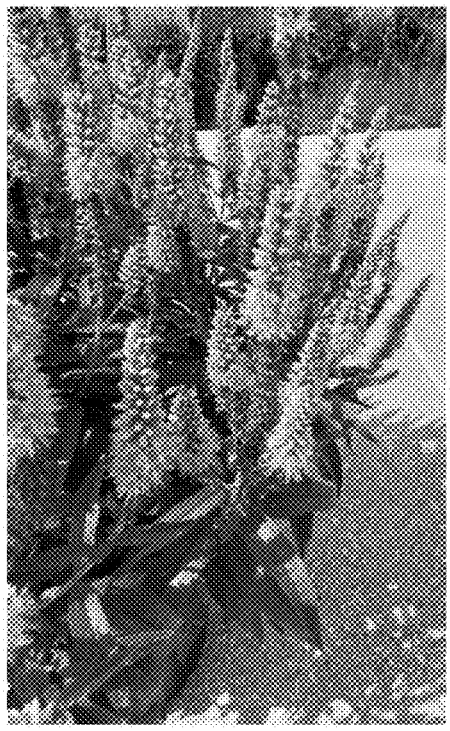
FIG. 2 illustrates a close-up view of the inflorescences of 'Balskywlipi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2025 under natural light conditions in West Chicago, Illinois.

The following descriptions and measurements describe approximately six-month-old plants produced from cuttings from stock plants and grown under conditions comparable to those used in commercial practice. The plants were grown as three plants per pot in one-gallon containers for approximately 10 weeks in a greenhouse in West Chicago, Illinois followed by 3.5 months in an outdoor nursery in West Chicago, Illinois. Plants were given one pinch three weeks before transplant and one pinch three weeks after transplant. Greenhouse temperatures ranged from an average high of 77.9° F. (25.5° C.) to an average low of 55.9° F. (13.3° C.). No supplemental lighting was provided. Measurements and numerical values represent averages of typical plants.

Botanical classification: *Veronica* hybrid 'Balskywlipi'.

Parentage:

*Female parent*.—Proprietary *Veronica spicata* breeding selection, coded X14-6480-004, unpatented.

*Male parent*.—*Veronica spicata* 'First Love', U.S. Plant Pat. No. 21,478.

Propagation:

*Type cutting*.—Terminal stem.

*Time to initiate roots*.—Approximately 7 to 10 days.

*Time to produce a rooted cutting*.—Approximately 35 to 42 days.

*Root description*.—Fibrous.

*Rooting habit*.—Freely branching.

Plant description:

*Commercial crop time*.—Approximately 10 to 12 weeks from a rooted cutting to finish in a 15 cm pot. Vernalization to initiate flowering is not required.

*Growth habit and general appearance*.—Herbaceous perennial, moderately vigorous, compact, upright-mounded.

*Hardiness*.—USDA Zone 4b (−25° F. to −20° F./−31.7° C. to −28.9° C.).

*Size*.—Height from soil level to top of plant plane: Approximately 45.0 cm. Width: Approximately 46.0 cm.

*Branching habit*.—Freely branching, pinching enhances basal branching. Quantity of main branches per plant: Approximately 8.

*Branch*.—Strength: Moderate. Branch height to bottom of inflorescence: Approximately 26.0 cm. Diameter: Approximately 6.0 mm. Length of central internode: Approximately 2.4 cm. Texture: Moderately pubescent. Color of young stems: 144B. Color of mature stems: 144B, becoming woody with an overlay of N199C with age.

Foliage description:

*General description*.—Quantity of leaves per main branch: Approximately 10. Fragrance: None detected. Form: Simple. Arrangement: Opposite, decussate.

*Leaves*.—Aspect: Perpendicular to stem. Shape: Lanceolate. Margin: Serrate. Apex: Acute to broadly acute. Base: Attenuate. Venation pattern: Pinnate. Length of mature leaf: Approximately 11.0 cm. Width of mature leaf: Approximately 3.5 cm. Texture of upper surface: Sparsely pubescent. Texture of lower surface: Sparsely pubescent and moderately pubescent on venation. Color of upper surface of young and mature foliage: Closest to 137A. Color of lower surface of young and mature foliage: Closest to 137C. Venation of upper and lower surface: 145A.

*Petioles*.—Length: Approximately 1.5 cm. Width: Approximately 4.0 mm. Texture: Sparsely pubescent. Color: 145B.

Flowering description:

*Flowering habit*.—'Balskywlipi' is a long-day obligate, freely flowering under outdoor growing conditions blooming from early spring through autumn.

*Lastingness of individual flower on the plant*.—Approximately 7 days.

Inflorescence description:

*General description*.—Type: Terminal raceme, self-cleaning. Fragrance: None detected. Height: Approximately 9.0 cm to 19.0 cm. Width: Approximately 1.5 cm to 2.0 cm. Quantity per plant: Approximately 50.

*Peduncle*.—Strength: Strong. Aspect: Erect. Length: Approximately 2.5 cm to 6.0 cm. Diameter: Approximately 1.5 mm to 2.5 mm. Texture: Densely pubescent. Color: 144A.

Flower description:

*General description*.—Type: Single, salverform. Aspect: Outward. Quantity per inflorescence: Approximately 90.

*Bud*.—Rate of opening: Generally, takes 3 to 4 days for bud to progress from first color to fully open flower.

*Bud just before opening*.—Shape: Oblong. Length: Approximately 5.0 mm. Diameter: Approximately 2.0 mm. Texture: Glabrous. Color: 65B with NN 155A at base.

*Corolla*.—Height: Approximately 6.5 mm. Diameter: Approximately 7.0 mm.

*Petals*.—Quantity: 4. Appearance: Dull. Shape: Obelliptic. Margin: Entire, wavy. Apex: Broadly acute. Base: Fused into tube. Length: Approximately 5.0 mm. Width: Approximately 2.0 mm. Texture of upper and lower surfaces: Glabrous. Color of upper and lower surfaces when first open: 65B. Color of upper and lower surfaces when fully open 65B to 65C.

*Corolla tube*.—Length: Approximately 2.0 mm. Diameter at tube opening: Approximately 1.5 mm. Texture of inner surface: Densely pubescent. Color of pubescence: NN155D. Texture of outer surface: Glabrous. Color of inner surface: 65D. Color of outer surface: 65D.

*Calyx*.—Shape: Cupped. Length: Approximately 2.0 mm. Diameter: Approximately 2.5 mm.

*Sepals*.—Quantity per flower: 4. Shape: Lanceolate, fused at base. Apex: Acute. Length: Two larger sepals approximately 3.0 mm and two smaller sepals approximately 2.0 mm. Width of all sepals: Approximately 1.0 mm. Texture of upper (inner) surface: Glabrous. Texture of lower (outer) surface: Moderately pubescent and densely pubescent on margins. Color of upper and lower surfaces: 137B.

*Pedicel*.—Strength: Strong, flexible. Aspect: Approximately 45° angle from peduncle. Length: Approximately 1.0 mm. Diameter: Approximately 0.5 mm. Texture: Densely pubescent. Color: 146B.

*Reproductive organs*.—Androecium: Stamen quantity: 2 per flower. Stamen length: Approximately 7.0 mm. Filament color: 65C. Anther shape: Sagittate, dorsifixed. Anther length: Approximately 1.0 mm. Anther color: 70A. Pollen amount: Moderate. Pollen color: 2D. Gynoecium: Pistil quantity: 1 per flower. Pistil length: Approximately 0.5 cm. Stigma shape: Rounded. Stigma length: Less than 1.0 mm. Stigma color: 71A. Style length: Approximately 4.0 mm. Style color: 71B. Ovary diameter: Approximately 1.0 mm. Ovary color: 145A.

Seed and fruit production: Neither seed nor fruit production has been observed.

Disease and pest resistance: Good resistance to powdery mildew observed.

What is claimed is:

1. A new and distinct cultivar of *Veronica* plant named 'Balskywlipi', substantially as herein illustrated and described.

* * * * *